United States Patent [19]

Cherkofsky

[11] 4,302,461

[45] Nov. 24, 1981

[54] ANTIINFLAMMATORY 5-SUBSTITUTED-2,3-DIARYLTHIOPHENES

[75] Inventor: Saul C. Cherkofsky, Wilmington, Del.

[73] Assignee: E. I. Du Pont de Nemours and Company, Wilmington, Del.

[21] Appl. No.: 159,236

[22] Filed: Jun. 20, 1980

Related U.S. Application Data

[63] Continuation-in-part of Ser. No. 65,069, Aug. 9, 1979, abandoned.

[51] Int. Cl.³ .................. A61K 31/44; A61K 31/38; C07D 409/04; C07D 333/34

[52] U.S. Cl. ................... 424/263; 424/275; 546/256; 546/284; 549/62; 549/80

[58] Field of Search ............... 549/62, 80; 424/275, 424/263; 546/256, 284

[56] References Cited

U.S. PATENT DOCUMENTS

| | | | |
|---|---|---|---|
| 2,639,286 | 5/1953 | Mavity | 549/86 |
| 3,531,497 | 9/1970 | Youngdale | 424/275 |
| 3,644,399 | 2/1972 | Brown et al. | 424/275 |

*Primary Examiner*—Natalie Trousof
*Assistant Examiner*—L. Hendriksen

[57] ABSTRACT

Antiinflammatory 5-substituted-2,3-diarylthiophenes, such as 2,3-bis(4-fluorophenyl)-5-(trifluoromethylthio)-thiophene, useful for treating arthritis and related diseases.

36 Claims, No Drawings

AlCl$_3$, is reacted with an alkanoic acid chloride to give a compound of structure I (R$^5 \neq$ H).

Compounds of structure I (R$^5$=H) are prepared by the reaction of a desoxybenzoin with the Vilsmeier reagent (dimethylformamide/phosphorous oxychloride)

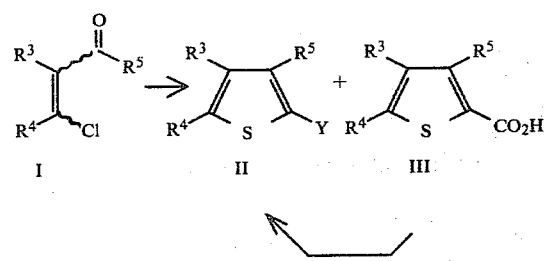
(2)

A compound of structure I is reacted with mercaptoacetic acid in pyridine in the presence of triethylamine to give thiophene II (Y=H). The by-product carboxylic acid (III) produced in the reaction is converted to II (Y=H) by heating at reflux in quinoline in the presence of copper powder.

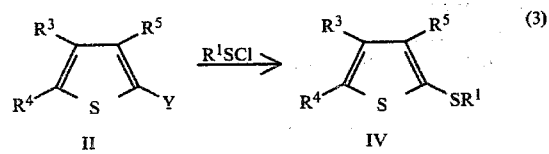
(3)

A 2,3-diarylthiophene (II, Y=H) in an inert solvent, e.g., methylene chloride, in the presence of an acid catalyst, e.g., stannic chloride or trifluoroacetic acid, is reacted with an alkylsulfenyl halide to give compound IV. The reaction can be carried out at a temperature from −78° to 100° C., although −20° C. to room temperature is preferred.

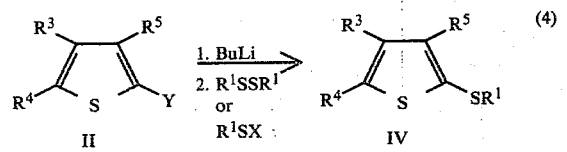
(4)

A 2,3-diarylthiophene (II; Y=H, Br) is reacted with a strong base such as n-butyl lithium or t-butyl lithium in an inert solvent such as tetrahyrofuran, diethyl ether or toluene, optionally in the presence of a complexing agent such as tetramethylethylenediamine and then treated with an alkylsulfenyl halide or disulfide to give compound IV. The reaction can be carried out at temperatures from −78° to 100° C.

2-Bromo-4,5-diarylthiophenes (II, Y=Br) are prepared by reaction of a 2,3-diarylthiopene (II=Y=H) with bromine (1 equivalent) in a solvent such as methylene chloride, acetic acid or their mixture at a temperature from −20° to 30° C.

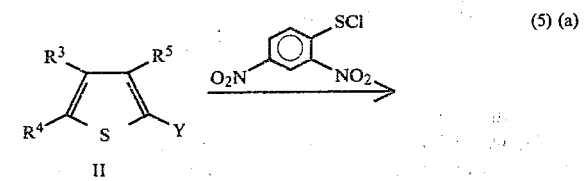
(5) (a)

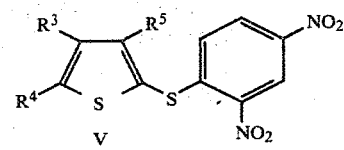
(5) (b)

A 2,3-diarylthiophene (II, Y=H) is reacted with 2,4-dinitrobenzenesulfenyl chloride in refluxing trifluoroacetic acid. The resultant 2,3-diaryl-5-(2,4-dinitrophenylthio)thiophene (V) is reacted with an alkylating agent to provide compound VI. The reaction is carried out in the presence of a base such as potassium hydroxide in a solvent mixture such as tetrahydrofuran, methanol and water. Within the context of the invention, tetrafluoroethylene and other fluorinated olefins used are considered alkylating agents as are dimethyl sulfate and alkyl halides and sulfonates.

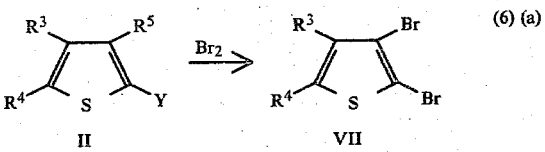
(6) (a)

A 2,3-diarylthiophene (II) (Y, R$^5$=H) is reacted with bromine (2 equivalents) in a solvent mixture such as methylene chloride and acetic acid at a temperature from 0° to 55° C. to give a dibromothiophene of structure VII.

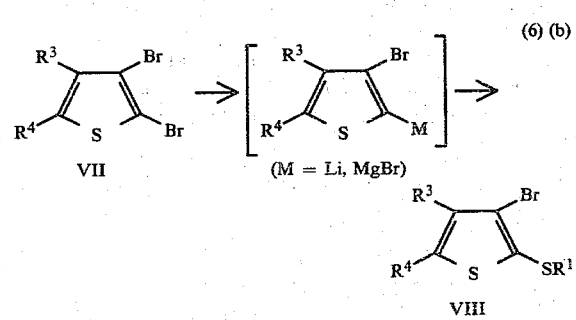
(6) (b)

A dibromothiophene (VII) in a solvent such as diethyl ether or tetrahydrofuran at a temperature from −78° to 35° C. is metallated with a reagent such as n-butyl lithium or magnesium to give an intermediate which is either (a) reacted with an alkylsulfenyl halide or disulfide at a temperature from −78° to 35° C. to give a compound of structure VIII or (b) treated with sulfur followed by reaction with an alkylating agent as defined in reaction (5) (b) at a temperature from −78° to 70° C. to provide a compound of structure VIII.

ANTIINFLAMMATORY 5-SUBSTITUTED-2,3-DIARYLTHIOPHENES

CROSS-REFERENCE TO RELATED APPLICATIONS

This application is a continuation-in-part of application Ser. No. 065,069, filed Aug. 9, 1979, now abandoned.

BACKGROUND OF THE INVENTION

This invention relates to antiinflammatory diaryl thiophenes.

A number of references, such as *Compt. Rend.*, 242, 1738 (1956) and *Z. Chem.*, 13, 57 (1973), disclose 2,3-diarylthiophenes.

Haas and Hellwig in *Chem. Ber.*, 109, 2475 (1976) disclose the reactions of alkylthiophenes and of halothiophenes with haloalkyl sulfenyl halides.

Schuetz and Fredericks in *J. Org. Chem.*, 27, 1301 (1962) disclose the reactions of alkylthiophenes with 2,4-dinitrobenzenesulfenyl chloride. They also describe solvolysis of the resulting sulfide to give the corresponding mercaptan.

Relyea et al., in German Pat. No. 27 24 494, disclose 2,3-diaryl-(5-arylthio)thiophenes and their use as insecticides and miticides.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new antiarthritic compounds with good antiinflammatory activity and minimal side effects that could be more effective in treating arthritis than presently available drugs.

SUMMARY OF THE INVENTION

This invention relates to novel antiinflammatory compounds, pharmaceutical compositions containing them, and methods of using them to treat arthritis in mammals. These compounds are of the formula:

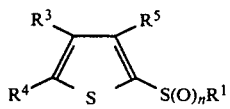

where
$R^1$ = mono- or polyfluoro $C_1$–$C_6$ alkyl or $C_1$–$C_6$ alkyl;
n = 0, 1 or 2;
$R^3$ and $R^4$ independently = pyridyl or

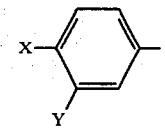

X = H, F, Cl, Br, $NO_2$, $C_1$–$C_2$ alkyl, $C_1$–$C_2$ alkoxy, di($C_1$–$C_2$ alkyl)amino or $S(O)_m R^2$; where
m = 0, 1 or 2; and
$R^2$ = $CH_3$ or $C_2H_5$;
Y = H, F or Cl
with the proviso that when Y is F or Cl, then X is F or Cl;
$R^5$ = H, $C_1$–$C_4$ alkyl or allyl;
provided
(a) when $R^1$ = $C_1$–$C_6$ alkyl, $R^3$ and $R^4$ cannot both be phenyl, or
(b) when n = 2, $R^3$ and $R^4$ cannot both be phenyl.

PREFERRED COMPOUNDS

Preferred compounds for utility considerations, and/or ease of synthesis are where, independently:
$R^1$ = $CF_3$; or
$R^5$ = H; or
n = 0 or 2; or
$R^3$ and $R^4$ independently =

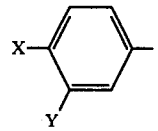

where
X = F, Cl, $OCH_3$ or $S(O)_m R^2$ and
Y = H.
More preferred definitions for $R^3$ and $R^4$ are where
X = $S(O)_m R^2$;
m = 0 or 2;
$R^2$ = $CH_3$ or $CH_2CH_3$; and
Y = H.
Examples of preferred compounds are
2,3-bis(4-fluorophenyl)-5-(trifluoromethylthio)thiophene;
2-(4-fluorophenyl)-3-(4-chlorophenyl)-5-(trifluoromethylthio)thiophene;
2-(4-fluorophenyl)-3-(4-methylthiophenyl)-5-(trifluoromethylthio)thiophene;
2-(4-methylthiophenyl)-3-(4-fluorophenyl)-5-(trifluoromethylthio)thiophene.

SYNTHESIS

The compounds of the invention can be made by the following reactions:

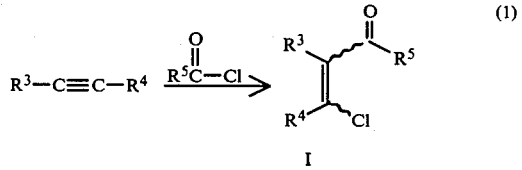

A diaryl acetylene in an inert solvent e.g., $CH_2Cl_2$ or $CCl_4$, in the presence of a Lewis acid catalyst, e.g.,

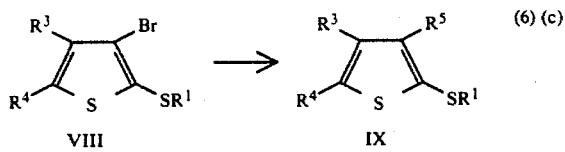

A compound of structure VIII in an inert solvent such as tetrahydrofuran or diethyl ether at a temperature from −78° to 70° C. is metallated with a lithium reagent such as n-butyl lithium or t-butyl lithium and then treated with an alkyl halide or sulfonate to give a compound of structure IX.

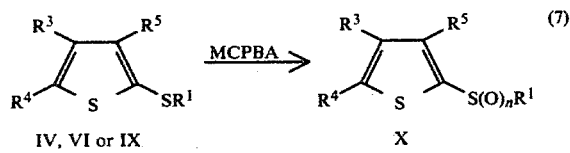

The 5-(substitutedthio)thiophenes from reactions 3, 4, 5 or 6 can then be oxidized to the corresponding sulfoxide or sulfone using m-chloroperbenzoic acid (MCPBA). Other suitable oxidizng agents include sodium metaperiodate, hydrogen peroxide and potassium permanganate.

Reaction 3 is the preferred method of preparation for compound VI where $R^5$=H and $R^1$=$CF_3$. Reaction 5 is the preferred method of preparation for compound VI where $R^5$=H and $R^1$=$C_1$-$C_6$ alkyl or mono or polyfluoro $C_1$-$C_6$ alkyl.

The compounds of the invention and their synthesis are illustrated further by the following examples. All temperatures are in degrees Centigrade.

EXAMPLE 1

2,3-bis(4-Fluorophenyl)-5-(trifluoromethylthio)thiophene

A solution of 2,3-bis(4-fluorophenyl)thiophene (5.4 g, 20 mmoles) in 30 ml methylene chloride and 30 ml trifluoroacetic acid was cooled to ≃−30° under $N_2$ and treated with trifluoromethane sulfenyl chloride (3.3 g., 24 mmoles) as a gas. The reaction mixture was stirred for 7 hours at 0° and then overnight at room temperature.

The reaction mixture was then purged with $N_2$ and concentrated in vacuo. The blue green residue was dissolved in methylene chloride and the resultant solution washed 3 times with saturated aqueous $NaHCO_3$, once with brine, dried and concentrated on a rotary evaporator. Crystallization from ethanol/water gave the title compound (5.9 g), m.p. 65°–8°. Infrared, and proton and fluorine NMR spectra were consistent with the assigned structure. MS 372 (M+)

Anal. Calcd. for $C_{17}H_9F_5S_2$: C, 54.82: H, 2.43. Found: C, 54.65; H, 2.64.

EXAMPLE 2

2,3-bis(4-Fluorophenyl)-5-(trifluoromethylsulfonyl)thiophene

A solution of 2,3-bis(4-fluorophenyl)-5-(trifluoromethylthio)thiophene (2.22 g, 6 mmoles) and m-chloroperbenzoic acid (2.68 g, 13.2 mmoles) in 50 ml toluene was heated at 50° for 5 hours. An additional portion of m-chloroperbenzoic acid (2.68 g, 13.2 mmoles) was added and the reaction heated at 60° for 13 hours. The reaction mixture was cooled and filtered. The filtrate was washed three times with saturated aqueous $NaHCO_3$, once with brine, dried and concentrated in vacuo. Recrystallization from ethanol/water gave the title compound (1.95 g), m.p. 104°–6°. Infrared and proton and fluorine NMR spectra were consistent with the assigned structure. MS 404 (M+)

Anal. Calcd. for $C_{17}H_9F_5O_2S_2$: C, 50.49; H, 2.24. Found: C, 50.35; H, 2.20.

EXAMPLE 3 a. 2,3-bis(4-Methoxyphenyl)-5-(2,4-dinitrophenylthio)thiophene

A suspension of 2,3-bis(4-methoxyphenyl)thiophene (6.6 g, 22.3 mmoles) and 2,4-dinitrobenzenesulfenyl chloride (5.5 g, 22.3 mmoles) in 55 ml of trifluoroacetic acid was heated at reflux for 15 minutes. The reaction mixture was cooled in ice; the lustrous crystals were collected and washed with cold ether to give the title compound (9.4 g), m.p. 143°–145° b. 2,3-bis(4-Methoxyphenyl)-5-(methylthio)thiophene

A suspension of 2,3-bis(4-methoxyphenyl)-5-(2,4-dinitrophenylthio)thiophene (4.8 g, 9.7 mmoles) in 20 ml $N_2$-purged methanol was cooled to 0° and treated with methyl iodide (1 ml, 14.6 mmoles) and a $N_2$-purged solution of potassium hydroxide (1.3 g, 19.4 mmoles) in a mixture of 5 ml water and 5 ml methanol. $N_2$-purged tetrahydrofuran (25 ml) was added and the reaction heated at reflux for 0.5 hour. An additional portion of methyl iodide (1 ml, 14.6 mmoles) was added and heating continued for 0.5 hour. The reaction mixture was cooled, poured into ≃50 ml 1 N HCl and extracted three times with ether and three times with ethyl acetate. The combined organic extracts were washed once with water, once with brine, dried and concentrated to a dark oil. Chromatography on silica gel and recrystallization from methanol gave the title compound (1.39 g), m.p. 106°–8°. Infrared and H-NMR spectra were consistent with the assigned structure. MS 342 (M+)

Anal. Calcd. for $C_{19}H_{18}S_2O_2$: C, 66.63; H, 5.30. Found: C, 66.82; H, 5.39.

EXAMPLE 4

2,3-bis(4-Methoxyphenyl)-5-(1,1,2,2-tetrafluoroethylthio)thiophene 2,3-bis(4-Methoxyphenyl)-5-(2,4-dinitrophenylthio)thiophene (4.9 g, 10 mmoles), tetrahydrofuran (60 ml), methanol/water (7.5 ml, 2.5 ml) and potassium hydroxide (1.3 g, 20 mmoles) were charged into a stainless steel bomb. The bomb was briefly evacuated, charged with tetrafluoroethylene (5 g, 50 mmoles) and agitated for 12 hours at room temperature. The reaction mixture was filtered and the filtrate concentrated to near dryness. The residue was taken up in ethyl acetate and filtered. The filtrate was washed three times with 1 N NaOH, three times with 1 N HCl, once with brine, dried and concentrated in vacuo. Crystallization from ethanol/water gave the title compound (2.4 g), m.p. 84°–7° (D). Infrared and H-NMR spectra were consistent with the assigned structure. MS 428 (M+)

Anal. Calcd. for $C_{20}H_{16}F_4O_2S_2$: C, 56.06; H, 3.76. Found: C, 56.1; H, 3.82.

The following compounds can be prepared following the procedures outlined above and illustrated in the preceeding examples.

TABLE 1

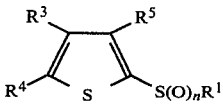

| Example No. | $R_1$ | $R_3$ | $R_4$ | $R_5$ | n | melting point °C. |
|---|---|---|---|---|---|---|
| 1 | $CF_3$ | 4-FPh | 4-FPh | H | 0 | 65–68 |
| 2 | $CF_3$ | 4-FPh | 4-FPh | H | 2 | 104–106 |
| 3 | $CH_3$ | 4-$CH_3$OPh | 4-$CH_3$OPh | H | 0 | 106–108 |
| 4 | $CF_2CF_2H$ | 4-$CH_3$OPh | 4-$CH_3$OPh | H | 0 | 84–87 (D) |
| 5 | $CF_3$ | Ph | Ph | H | 0 | 70–72 |
| 6 | $CF_3$ | 4-$CH_3$OPh | 4-$CH_3$OPh | H | 0 | 114–116 (D) |
| 7 | $CF_3$ | 4-ClPh | 4-FPh | H | 0 | 67–69 |
| 8 | $CH_3$ | 4-FPh | 4-FPh | H | 0 | 91–93 |
| 9 | $CF_3$ | 4-FPh | 4-ClPh | H | 0 | 66–69 |
| 10 | $CF_2CF_2H$ | 4-FPh | 4-FPh | H | 0 | 56–57 |
| 11 | $CF_2CF_2H$ | 4-$CH_3$OPh | 4-$CH_3$OPh | H | 2 | 106–109 |
| 12 | $CF_2CF_2H$ | 4-FPh | 4-FPh | H | 2 | 104–106 |
| 13 | allyl | 4-$CH_3$OPh | 4-$CH_3$OPh | H | 0 | |
| 14 | $CF_3$ | Ph | 3,4 diClPh | H | 0 | |
| 15 | $CF_3$ | Ph | 3,4 diClPh | H | 1 | |
| 16 | $nC_4H_9$ | 4-FPh | 4-FPh | H | 0 | |
| 17 | $CF_3$ | 4-ClPh | 4-FPh | H | 1 | |
| 18 | $CF_2CF_2H$ | 4-$CH_3$OPh | 4-$CH_3$OPh | H | 1 | |
| 19 | $CH_2CH_2CH_2CF_3$ | 4-FPh | 4-FPh | H | 0 | |
| 20 | $nC_6H_{13}$ | 4-$CH_3$OPh | 4-$CH_3$OPh | H | 0 | 52–55 |
| 21 | $CF_3$ | 4-$CH_3$OPh | 4-$CH_3SO_2$Ph | H | 0 | 125–127 |
| 22 | $CF_3$ | 4-FPh | 4-$CH_3$SPh | H | 0 | 66–69 |
| 23 | $CF_3$ | 4-FPh | 4-$CH_3$SOPh | H | 0 | |
| 24 | $CF_3$ | 4-$CH_3$SPh | 4-FPh | H | 0 | 62–65 |
| 25 | $CF_3$ | 3-pyridyl | 4-FPh | H | 0 | |
| 26 | $CF_3$ | 4-FPh | 4-FPh | $CH_3$ | 0 | |
| 27 | $CF_3$ | 4-$CH_3$Ph | 4-$CH_3$Ph | H | 0 | |
| 28 | $CF_3$ | 4-$NO_2$PH | 4-FPh | H | 0 | |
| 29 | $CF_3$ | 4-$(CH_3)_2$NPh | 4-FPh | H | 0 | |
| 30 | $CF_3$ | 4-$C_2H_5$OPh | 4-$C_2H_5$SPh | H | 0 | |
| 31 | $CF_3$ | 4-FPh | 4-$CH_3$SPh | $C_2H_5$ | 0 | |
| 32 | $CF_3$ | 4-FPh | 4-BrPh | $CF_3$ | 0 | |
| 33 | $CF_3$ | 4-FPh | 4-FPh | allyl | 0 | |
| 34 | $CF_3$ | 4-FPh | 4-FPh | $nC_4H_9$ | 0 | |
| 35 | $CF_3$ | 4-FPh | 4-FPh | $iC_3H_7$ | 0 | |

DOSAGE FORMS

The antiarthritic agents of this invention can be administered to treat arthritis by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 40 milligrams per kilogram of body weight. Ordinarily 0.05 to 20, and preferably 0.1 to 4 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben and chlorobutanol.

Suitable pharmaceutical carriers are described in Remington's Pharmaceutical Sciences, E. W. Martin, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by filtration.

SUSPENSION

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

INJECTABLE

A parenteral composition suitable for administration by injection is prepared by stirring 1% by weight of active ingredient in sodium chloride injection U.S.P. XV and sterilizing by filtration.

USE

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2, 1973, "Models Used for the Study and Therapy of Rheumatoid Arthritis'-'—Symposium of the American Society for Pharmacology and Experimental Therapeutics—states "The rat polyarthritis produced by intradermal injection of a suspension of Mycobacterium tuberculosis in mineral oil (adjuvant) has been used extensively for the screening of drugs of potential use in rheumatoid arthritis."

Compounds of this invention have shown activity in adjuvant-induced arthritis in rats which is widely recognized as a good model of human rheumatoid arthritis.

METHODS

Established Adjuvant-Induced Arthritis in Rats

Lewis (Wistar) male rats (Charles River Breeding Laboratories, Wilmington, Mass.) weighing 175–220 grams were injected subcutaneously with 0.1 ml of adjuvant in the plantar area of the right hind paw. The adjuvant was prepared by bead-milling, heat-killed, lyophilized Mycobacterium butyricum (Difco #0640) in light mineral oil (Fisher Scientific Co. #0-119 Paraffin Oil—Saybolt Viscosity 125/135) 5 mg/ml. Twenty non-arthritic control rats were injected with mineral oil. The animals received water and Wayne Lab-Blox ad libitum*.

*while on a 10-hour light—14 hour-dark cycle

The rats were held for 14 days to allow the development of polyarthritis. The volume of the uninjected, left-hind paw of each rat was measured by using a Ugo Basile Volume Differential Meter, Model 7101. Adjuvant injected rats showing no evidence of arthritis were discarded and the arthritic rats were distributed into groups of 10 having equal mean paw volumes with equal standard deviation. Non-arthritic (oil-injected) control rats were distributed to 2 groups of 10. Suspensions of test compounds were prepared for dosing by bead-milling (4 mm glass beads in rubber stoppered serum bottles) for 4–5 hours in aqueous 1% polyvinyl alcohol, 5% gum acacia and 0.5% methylparaben.

Test compounds were given orally by gavage once daily for 7 days (days 14–20). The 2 groups of oil injected, non-arthritic control rats and the 2 groups of arthritic control rats received vehicle only for 7 days. Paw volumes (uninjected left hind paw) were measured 20 hours after the last dose (on day 21).

Percent decrease from control mean paw volume was calculated with the following formula:

$$\frac{\text{Arthritic Vehicle Control Mean Paw Volume (ml)} - \text{Arthritic Treatment Mean Paw Volume (ml)}}{\text{Arthritic Vehicle Control Mean Paw Volume (ml)} - \text{Non-Arthritic Vehicle Control Mean Paw Volume (ml)}} \times 100 =$$

% Decrease from Control Mean Paw Volume

Dose-response regression lines of the % decrease were ploted on semi-log paper and the $ED_{50}\%$ for decrease from control paw volume was estimated by inspection.

RESULTS

TABLE 2

| Compound Example No. | Daily Oral Dose mg/kg | Percent Decrease from Control Paw Volume* |
|---|---|---|
| 3 | 27 | 43[4] |
| 4 | 27 | 11[1] |
| 5 | 20 | 33[3] |
| 6 | 20 | 32[3] |
| 8 | 27 | 25[2] |
| 10 | 27 | 28[4] |
| 11 | 27 | 23[3] |
| 12 | 27 | 34[3] |

TABLE 2-continued

| Compound Example No. | Daily Oral Dose mg/kg | Percent Decrease from Control Paw Volume* |
|---|---|---|
| 20 | 81 | 39[5] |

*[1] $p > 0.1$ compared to control by Student's "t" test
[2] $p < 0.1$ compared to control by Student's "t" test
[3] $p < 0.05$ compared to control by Student's "t" test
[4] $p < 0.01$ compared to control by Student's "t" test
[5] $p < 0.001$ compared to control by Student's "t" test

TABLE 3

| Compound Example No. | ED$_{50}$ % Decrease From Control Paw Volume mg/kg |
|---|---|
| 1 | 3.5 |
| 2 | 10 |
| 7 | 4 |
| 9 | 10 |
| 21 | 9 |
| 22 | 0.4 |
| 24 | 0.15 |
| Indomethacin | 0.25 |
| Phenylbutazone | 10 |
| Aspirin | 270 |

Note—The Example 4 compound did not exhibit statistically significant antiinflammatory activity at the dose level tested but it is considered to have antiinflammatory activity at higher dose levels.

It is shown in Table 2 above that compounds of this invention are much more potent than aspirin and phenylbutazone and about as potent as indomethacin in the treatment of rat arthritis.

What is claimed is:

1. A compound of the formula:

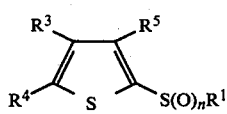

where
R$^1$ = mono- or polyfluoro C$_1$-C$_6$ alkyl or C$_1$-C$_6$ alkyl;
n = 0, 1 or 2;
R$^3$ and R$^4$ independently = pyridyl or

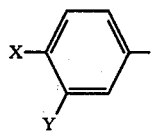

X = H, F, Cl, Br, NO$_2$, C$_1$-C$_2$ alkyl, C$_1$-C$_2$ alkoxy, di(C$_1$-C$_2$ alkyl)amino, or S(O)$_m$R$^2$; where
m = 0, 1 or 2; and
R$^2$ = CH$_3$ or C$_2$H$_5$;
Y = H, F or Cl with the proviso that when Y is F or Cl, then X is F or Cl;
R$^5$ = H, C$_1$-C$_4$ alkyl or allyl; provided
(a) when R$^1$ = C$_1$-C$_6$ alkyl, R$^3$ and R$^4$ cannot both be phenyl; or
(b) when n = 2, R$^3$ and R$^4$ cannot both be phenyl.

2. A compound of claim 1 where R$^1$ = CF$_3$.
3. A compound of claim 1 where R$^5$ = H.
4. A compound of claim 1 where n = 0 or 2.
5. A compound of claim 1 where R$^3$ and R$^4$ independently =

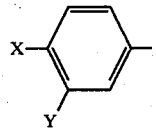

where
X = F, Cl, OCH$_3$ or S(O)$_m$R$^2$ and Y = H.

6. A compound of claim 1 where R$^3$ and R$^4$ independently =

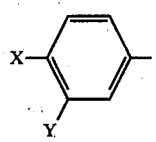

where
X = S(O)$_m$R$^2$,
m = 0 or 2,
R$^2$ = CH$_3$ or C$_2$H$_5$, and
Y = H.

7. A compound of claim 6 where R$^1$ = CF$_3$, n = 0 or 2, and R$^5$ = H.

8. A compound of claim 1 where R$^3$ and R$^4$ independently =

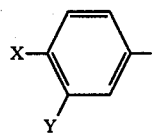

where
X = H, F, Cl, OCH$_3$, S(O)$_m$R$^2$;
m = 0, 1 or 2;
R$^2$ = CH$_3$ or C$_2$H$_5$;
Y = H or Cl provided Y cannot be Cl unless X is Cl,
R$^5$ = H.

9. The compound of claim 1 which is 2,3-bis(4-fluorophenyl)-5-(trifluoromethylthio)thiophene.

10. The compound of claim 1 which is 2-(4-fluorophenyl)-3-(4-chlorophenyl)-5-(trifluoromethylthio)thiophene.

11. The compound of claim 1 which is 2-(4-fluorophenyl)-3-(4-methylthiophenyl)-5-(trifluoromethylthio)thiophene.

12. The compound of claim 1 which is 2-(4-methylthiophenyl)-3-(4-fluorophenyl)-5-(trifluoromethylthio)thiophene.

13. A pharmaceutical composition consisting essentially of a suitable pharmaceutical carrier and an effective antiinflammatory amount of a compound of claim 1.

14. A pharmaceutical composition consisting essentially of a suitable pharmaceutical carrier and an effective antiinflammatory amount of a compound of claim 2.

15. A pharmaceutical composition consisting essentially of a suitable pharmaceutical carrier and an effective antiinflammatory amount of a compound of claim 3.

16. A pharmaceutical composition consisting essentially of a suitable pharmaceutical carrier and an effective antiinflammatory amount of a compound of claim 4.

17. A pharmaceutical composition consisting essentially of a suitable pharmaceutical carrier and an effective antiinflammatory amount of a compound of claim 5.

18. A pharmaceutical composition consisting essentially of a suitable pharmaceutical carrier and an effective antiinflammatory amount of a compound of claim 6.

19. A pharmaceutical composition consisting essentially of a suitable pharmaceutical carrier and an effective antiinflammatory amount of a compound of claim 7.

20. A pharmaceutical composition consisting essentially of a suitable pharmaceutical carrier and an effective antiinflammatory amount of a compound of claim 8.

21. A pharmaceutical composition consisting essentially of a suitable pharmaceutical carrier and an effective antiinflammatory amount of the compound of claim 9.

22. A pharmaceutical composition consisting essentially of a suitable pharmaceutical carrier and an effective antiinflammatory amount of the compound of claim 10.

23. A pharmaceutical composition consisting essentially of a suitable pharmaceutical carrier and an effective antiinflammatory amount of the compound of claim 11.

24. A pharmaceutical composition consisting essentially of a suitable pharmaceutical carrier and an effective antiinflammatory amount of the compound of claim 12.

25. A method of treating arthritis in a mammal which comprises administering to the mammal an effective antiarthritic amount of a compound of claim 1.

26. A method of treating arthritis in a mammal which comprises administering to the mammal an effective antiarthritic amount of a compound of claim 2.

27. A method of treating arthritis in a mammal which comprises administering to the mammal an effective antiarthritic amount of a compound of claim 3.

28. A method of treating arthritis in a mammal which comprises administering to the mammal an effective antiarthritic amount of a compound of claim 4.

29. A method of treating arthritis in a mammal which comprises administering to the mammal an effective antiarthritic amount of a compound of claim 5.

30. A method of treating arthritis in a mammal which comprises administering to the mammal an effective antiarthritic amount of a compound of claim 6.

31. A method of treating arthritis in a mammal which comprises administering to the mammal an effective antiarthritic amount of a compound of claim 7.

32. A method of treating arthritis in a mammal which comprises administering to the mammal an effective antiarthritic amount of a compound of claim 8.

33. A method of treating arthritis in a mammal which comprises administering to the mammal an effective antiarthritic amount of the compound of claim 9.

34. A method of treating arthritis in a mammal which comprises administering to the mammal an effective antiarthritic amount of the compound of claim 10.

35. A method of treating arthritis in a mammal which comprises administering to the mammal an effective antiarthritic amount of the compound of claim 11.

36. A method of treating arthritis in a mammal which comprises administering to the mammal an effective antiarthritic amount of the compound of claim 12.

* * * * *